United States Patent [19]

Hunter

[11] Patent Number: 4,496,483
[45] Date of Patent: Jan. 29, 1985

[54] N-HEXAMETHYLENEIMINO THIOLCARBAMATE COMPOUNDS

[75] Inventor: Don L. Hunter, Anaheim, Calif.

[73] Assignee: United States Borax & Chemical Corporation, Los Angeles, Calif.

[21] Appl. No.: 531,139

[22] Filed: Sep. 12, 1983

[51] Int. Cl.³ .................... A01N 47/12; C07D 295/00
[52] U.S. Cl. .................... 260/239 BF; 71/88; 570/135; 570/136; 570/189
[58] Field of Search .................. 260/239 BF; 546/244

[56] References Cited

U.S. PATENT DOCUMENTS

| 3,198,698 | 8/1965 | Reuter et al. | 546/244 |
| 3,357,815 | 12/1967 | D'Amico | 260/239 BF |
| 3,516,986 | 6/1970 | Hunter et al. | 260/239 BF |

Primary Examiner—Alton D. Rollins
Attorney, Agent, or Firm—James R. Thornton

[57] ABSTRACT

S-(2-Halo-2-propen-1-yl) N-(hexamethyleneimino)thiolcarbamates in which the halo is preferably bromo or chloro. The compounds have biological activity and may be used, for example, as selective pre-emergence herbicides.

5 Claims, No Drawings

N-HEXAMETHYLENEIMINO THIOLCARBAMATE COMPOUNDS

This invention relates to a novel class of thiolcarbamates and method for producing the compounds.

The compounds provided by this invention have the structure

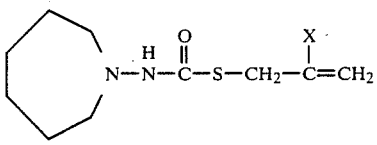

in which X represents halogen such as bromo, chloro and fluoro.

The novel thiolcarbamates of this invention can be prepared by reaction of the sodium salt of N-hexamethyleneimino thiolcarbamic acid with a 2,3-dihalo-1-propene. The sodium thiolcarbamate is readily prepared by reaction of N-aminohexamethyleneimine with carbonyl sulfide in the presence of an alkali metal hydroxide such as sodum hydroxide. The reactions may be illustrated by the following equations:

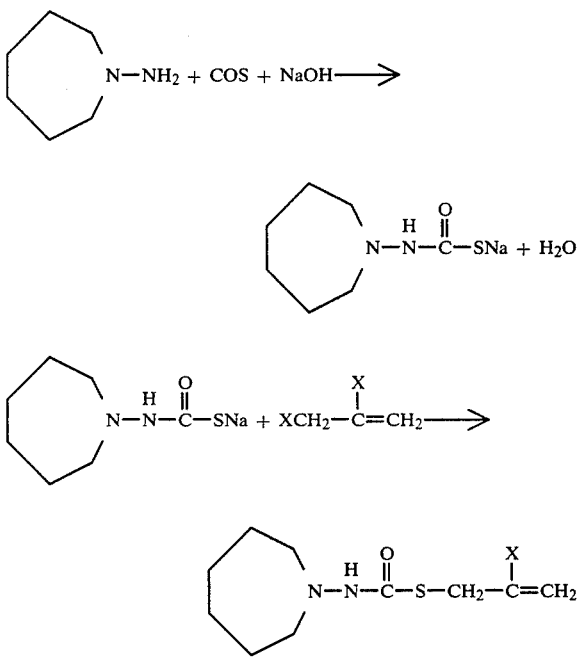

in which X represents a reactive halogen.

The initial reaction to form the sodium salt of the substituted carbamic acid takes place rapidly at low temperatures, preferably at temperatures below room temperature so as to provide adequate control of the reaction rate. Cold water is a suitable reaction medium. The subsequent reaction with the dihalopropene is also conducted at low temperatures such as in the presence of cold water. The resultant product may be extracted from the aqueous reaction mixture by means of an immiscible organic solvent such as benzene. Removal of the solvent, such as by evaporation under reduced pressure, gives the impure product which may be purified such as by recrystallization.

The compounds are generally crystalline solids which are soluble in organic solvents such as methanol, ethanol, benzene, hexane and acetone.

The following examples illustrate preparation of representative compounds of this invention.

EXAMPLE I

S-(2-Chloro-2-propen-1-yl) N-(hexamethyleneimino)thiolcarbamate

A 500 ml., 3-necked, round-bottom flask was fitted with a mechanical stirrer, a Dry Ice-acetone condenser, and a Dry Ice-acetone jacketed buret topped with a second Dry Ice condenser. A solution of 2.0 g. (0.05 mole) of sodium hydroxide pellets and 5.71 g. (0.05 mole) of N-aminohexamethyleneimine in 100 ml. of distilled water was placed in the flask. Carbonyl sulfide (2.5 ml.; 3.0 g.; 0.05 mole) was condensed into the addition buret and added dropwise to the stirred solution, with cooling of the flask in ice water. After one hour of stirring, the ice water bath was removed and 5.55 g. (0.05 mole) of 2,3-dichloro-1-propene added in one portion. The mixture was stirred at room temperature for 17 hours and the reaction mixture then extracted with 100 ml. of benzene. The benzene layer was separated and the solvent evaporated under reduced pressure. 100 ml. of absolute ethanol was added to the residue and then evaporated under reduced pressure to remove any residual moisture.

The residue was triturated with 50 ml. of cold ethanol and filtered through Celite to remove grease. The filtrate was evaporated under reduced pressure and the residue crystallized from hot hexane to give 2.93 g. (23.6%) of colorless crystals, m.p. 91°–93° C. After recrystallization from hexane, the product melted at 91.5°–92.5° C.

EXAMPLE II

S-(2-Bromo-2-propen-1-yl) N-(hexamethyleneimino)-thiolcarbamate is prepared in a similar manner by reaction of 2,3-dibromo-1-propene with the N-substituted sodium thiolcarbamate.

The compounds of this invention have biological activity; for example, they are useful as pre-emergence herbicides for controlling millet and similar grassy weeds in the presence of other desirable plants. The compound is applied to soil, preferably in diluted form, prior to emergence of the weeds at application rates in the range of from about 1 to about 10 pounds per acre. Millet and similar grassy weeds in the treated area are killed or severely injured prior to or immediately following emergence from the soil, without injury to desirable plants such as the broadleaf crop plants.

The following example illustrates the herbicidal activity of the present compounds.

EXAMPLE III

S-(2-Chloro-2-propen-1-yl) N-(hexamethyleneimino)-thiolcarbamate was evaluated as both a pre-emergence and post-emergence treatment. Greenhouse flats were planted to four representative grasses and four representative broad-leaf species. The flats were sprayed on the same day as planting with an ethanol solution of the compound at rates of 1.5, 3, 5 and 8 pounds per acre.

Another set of flats with the same plants was treated after the plants had emerged and were about one inch in height. These flats were also sprayed with an ethanol solution of the compound at rates of 1.5, 3, 5 and 8 pounds per acre. The flats were kept in the greenhouse and watered when needed. Thirty days after treatment the flats were examined and the plants rated for herbicidal activity on a 0 to 9 scale in which 0=no effect, 5=substantial injury with some kill, and 9=complete kill. The following results were obtained:

| | Activity Rating | | | | | | | |
|---|---|---|---|---|---|---|---|---|
| | Pre | | | | Post | | | |
| | Pounds Per Acre | | | | | | | |
| Test plant | 1.5 | 3 | 5 | 8 | 1.5 | 3 | 5 | 8 |
| Corn | 0 | 0 | 0 | 0 | 0 | 0 | 0 | 0 |
| Millet | 9 | 9 | 9 | 9 | 0 | 0 | 0 | 0 |
| Rye Grass | 0 | 0 | 0 | 0 | 0 | 0 | 0 | 0 |
| Oats | 0 | 0 | 0 | 0 | 0 | 0 | 0 | 0 |
| Peas | 0 | 0 | 0 | 0 | 0 | 0 | 0 | 0 |
| Mustard | 0 | 0 | 0 | 0 | 0 | 0 | 0 | 0 |
| Cucumber | 0 | 0 | 0 | 0 | 0 | 0 | 2 | 3 |
| Snap Beans | 0 | 0 | 0 | 0 | 0 | 0 | 0 | 0 |

Since a relatively small amount of one or more of the active compounds should be uniformly distributed over the area to be treated, they are preferably formulated with conventional herbicide carriers, either liquid or solid. Thus, the compound can be impregnated on or admixed with a pulverulent solid carrier such as lime, talc, clay, Bentonite, calcium chloride, vermiculite, calcium carbonate, and the like. Alternatively, the compound can be dissolved or suspended in a liquid carrier such as water, kerosene, alcohols, xylene, benzene, ketones, and the like. A surfactant is preferably included to aid dispersion, emulsification and coverage. The surfactant can be ionic or non-ionic, and may be a liquid or a solid. The use of the term "surfactant" herein is intended to include such compounds commonly referred to as wetting agents, dispersing agents and emulsifying agents. Typical surfactants include the alkylarylsulfonates, the fatty alcohol sulfates, sodium salt of naphthalenesulfonic acid, alkylaryl polyether alcohols, long chain quaternary ammonium compounds, sodium salts of petroleum-derived alkylsulfonic acids, polyoxyethylene-sorbitan monolaurate, and the like. These dispersing and wetting agents are sold under numerous trademarks and may either be pure compounds, mixtures of compounds of the same general group, or they can be mixtures of compounds of different classes. Surfactants can also be included in compositions containing a solid inert carrier.

Concentrated compositions containing the active agent which can be subsequently diluted, as with water, to the desired concentration for application to soil are also provided. The advantages of such concentrates are that they are prepared by the manufacturer in a form such that the user need only mix them with a locally available carrier, preferably water, thereby keeping shipping costs to a minimum while providing a product which can be used with a minimum of equipment and effort. Such concentrates may contain from about 5 to about 95 percent by weight of one or more of the active compounds with a carrier or diluent, which may be a liquid or a solid. Liquid carriers which are miscible with the active agent or other liquids in which the compound may be suspended or dispersed can be used. A surfactant is also generally included to facilitate such dilution or dispersion in water. However, the surfactant itself may comprise the carrier in such concentrates.

The herbicidal compositions can include other beneficial adjuvants, such as humectants, oils and contact agents. Also, other herbicides such as the sodium borates, sodium chlorate, substituted uracils and ureas, triazines, benzimidazoles, carbamates, anilides, amides, and haloalkanoic acids, can be included in the formulation.

Various changes and modifications of the invention can be made and, to the extent that such variations incorporate the spirit of this invention, they are intended to be included within the scope of the invention.

What is claimed is:

1. Thiolcarbamates of the formula

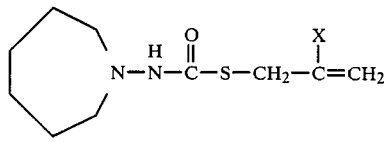

wherein X represents halogen.

2. A compound in accordance with claim 1 in which said X is bromine.

3. A compound in accordance with claim 1 in which said X is chlorine.

4. S-(2-Chloro-2-propen-1-yl) N-(hexamethyleneimino)-thiolcarbamate.

5. S-(2-Bromo-2-propen-1-yl) N-(hexamethyleneimino)-thiolcarbamate.

* * * * *